(12) United States Patent
Gouma et al.

(10) Patent No.: US 11,844,604 B1
(45) Date of Patent: Dec. 19, 2023

(54) METHOD FOR ANALYZING A SUBJECT'S BREATH

(71) Applicant: Ohio State Innovation Foundation, Columbus, OH (US)

(72) Inventors: Pelagia I. Gouma, Columbus, OH (US); Matthew Exline, Columbus, OH (US); Andrew Bowman, Milford Center, OH (US); Milutin Stanacevic, Smithtown, NY (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/089,251

(22) Filed: Dec. 27, 2022

Related U.S. Application Data

(63) Continuation of application No. PCT/US2022/016579, filed on Feb. 16, 2022.

(60) Provisional application No. 63/149,905, filed on Feb. 16, 2021.

(51) Int. Cl.
*A61B 5/08* (2006.01)
*G01N 33/497* (2006.01)

(52) U.S. Cl.
CPC ........... *A61B 5/082* (2013.01); *G01N 33/497* (2013.01); *G01N 2033/4977* (2013.01)

(58) Field of Classification Search
None
See application file for complete search history.

(56) References Cited

U.S. PATENT DOCUMENTS

2020/0229735 A1   7/2020   Muchmore

OTHER PUBLICATIONS

Gillogly (Wired Sep. 15, 2020, https://mse.osu.edu/news/2020/09/perena-goumas-breathalyzer-technology-featured-wired-covid-19-diagnostic-tool). (Year: 2020).*
International Searching Authority, International Search Report and Written Opinion issued in corresponding PCT Application No. PCT/US2022/016579, dated May 13, 2022.
Karimi et al., Single Exhale Biomarker Breathalyzer, Sensors 2019; vol. 19 No. 2, p. 270 (11 pages).
Gouma et al., Novel Isoprene Sensor for a Flu Virus Breath Monitor, Sensors 2017; vol. 17 No. 12. Page 199 www.mdpi.com/journal/sensors (7 pages).
Gouma et al., Nanosensor and Breath Analyzer for Ammonia Detection in Exhaled Human Breath, IEEE Sensors Journal, vol. 10, No. 1, Jan. 2010 (5 pages).
Exline, et al., Exhaled nitric oxide detection for diagnosis of COVID-19 I critically ill patients, PLoS ONE 16(10:e0257644, https://doi.org/10.1371/journal.pone.0257644, 2021 (7 pages).

* cited by examiner

*Primary Examiner* — Jay B Shah
(74) *Attorney, Agent, or Firm* — Wood Herron & Evans LLP

(57) ABSTRACT

A method for evaluating for the presence of the COVID disease by detecting one or more biomarkers using a breathalyzer (138). The breath sample (2) taken from the subject (10) is passed over a sensor (140) which changes resistance in the presence of nitric oxide as a function of concentration. The resistance pattern of the subject (10) having the COVID disease will have a distinct shape, approximating the appearance of the small Greek letter omega (ω). Test results can be generated in less than a minute.

14 Claims, 3 Drawing Sheets

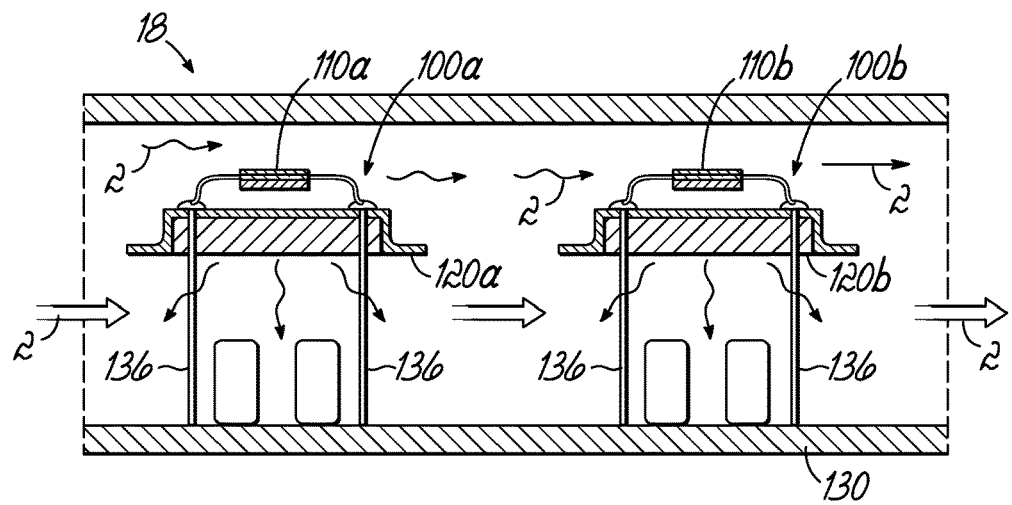
FIG. 3
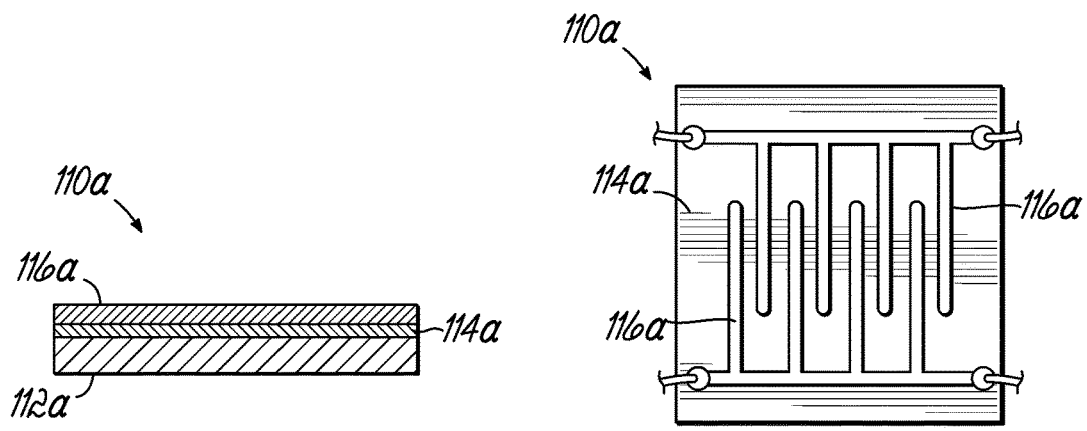
FIG. 3A
FIG. 3B
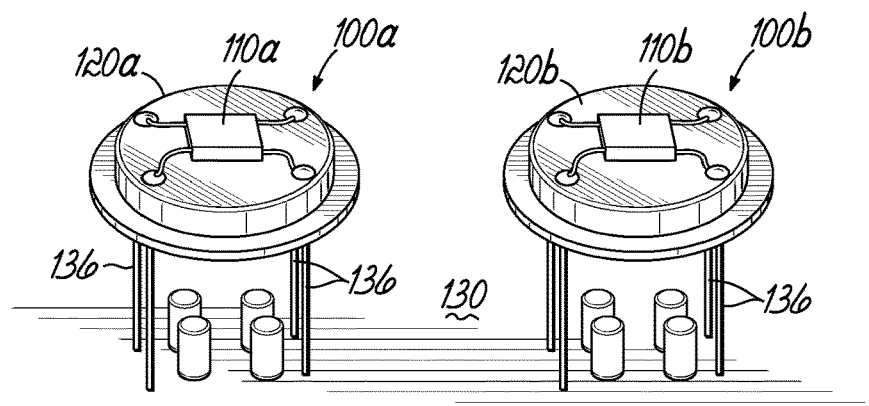
FIG. 4

METHOD FOR ANALYZING A SUBJECT'S BREATH

RELATED APPLICATION

This application is a continuation of International PCT Application No. PCT/US2022/016579 filed Feb. 16, 2022, entitled "METHOD FOR ANALYZING A SUBJECT'S BREATH", which claims priority to U.S. Provisional Patent Application No. 63/149,905 filed Feb. 16, 2021, entitled "METHOD FOR ANALYZING A SUBJECT'S BREATH", the disclosures of which are hereby incorporated by reference herein in their entireties.

STATEMENT OF FEDERALLY SPONSORED RESEARCH

This invention was made with government support under grant/contract number 2029847 awarded by National Science Foundation. The government has certain rights in the invention.

FIELD OF THE INVENTION

The present invention relates to a method for quickly and accurately evaluating a subject's exhaled breath for biomarkers which indicate the presence of a viral infection, such as the COVID-19 disease.

BACKGROUND OF THE INVENTION

The invention relates to a testing method for the presence of certain viruses in a mammal, as evidenced by the presence of certain gases in the subject's breath.

Significant infection events, such as the COVID-19 epidemic, require the need for accurate and fast test data to determine if a subject requires quarantining or treatment, to facilitate restoring the health of the subject and reduce the prospect of spreading the infection. Further, at the time a subject has been determined to have the COVID-19 disease, it is important to understand the progression of the illness which results from being infected with the beta coronavirus SARS-CoV-2, and its end-point.

Presently, testing for the COVID-19 disease virus is done in three ways. First, there is a molecular test; variously known as the PCR (polymerase chain reaction) test, a viral RNA test, or a nucleic acid test. This test is performed by first taking a nasal swab, throat swab, or test of saliva or other bodily fluids from the subject. This molecular test is typically conducted in a hospital, a medical office, or at mobile testing sites. The test evaluates for the presence of genetic material that can be obtained only from the virus. The test itself can generate results within a few hours in a best-case scenario, but the results often take at least a day or two to be processed and reported. Also, much longer turn-around times may occur, depending upon the efficiency and the volume of test procedures being run.

The molecular test is susceptible to providing false-negative results, i.e., a result which indicates that the subject does not have the virus when the virus is present, actually. In some instances, the false-negative rate can be 20% when testing is performed at least five days after the symptoms began. However, the false-negative rate can be much higher, even up to 100%, earlier in the lifetime of the infection against the subject. The test can also give false positive indications for a long time after the infected person has recovered due to the high sensitivity of the molecular test in detecting RNA fragments.

A second test is known as the antigen test, which is performed using a nasal or throat swab. The antigen test is used to identify protein fragments (antigens) from the virus in the subject. This test can be performed more quickly than a molecular test, sometimes with results available in only minutes. However, false-negative results tend to occur more often with antigen tests than with molecular tests. This is a reason why antigen tests are not favored by the FDA as a single test for active infection. One option is to perform repeated antigen tests of the same subject to evaluate the likelihood of infection. Again though, the false positive rate goal should be as close as possible to zero, and this is typically not the case with antigen testing.

Another test for COVID-19, though it is used to detect whether the subject previously had been infected with the virus, is an antibody test. This is conducted by taking a sample of blood from the subject, and would be performed typically in a doctor's office, hospital, or blood testing lab. Such a test cannot determine if the subject presently has the infection. However, it can accurately identify past infection. Results from the testing are typically available within a few days. The antibody test is also subject to a risk of a false negative because it typically takes a week or two after the infection for the subject's immune system to produce antibodies. The reported rate of false negatives typically runs around 20%.

SUMMARY OF THE INVENTION

To address the issue of COVID-19 test result delays and obviate the risk of false test results from either the molecular test or the antigen test, a test to evaluate for the presence of the COVID-19 disease in a subject is performed utilizing a breath analyzer unit (also identified herein as a breathalyzer). The breathalyzer is capable of performing an analysis of gaseous biomarkers from the test subject resulting from metabolic changes occurring in the body as a result of the infection by the virus. The unit detects gaseous biomarkers in a subject's breath which, in turn, would signal the presence and the severity of the infection caused by the SARS-CoV-2 virus.

Testing using the breathalyzer begins with the subject either providing a single breath exhale into the device, or alternatively exhaling into a breath bag which then provides an approximate six-hour lifetime of maintaining the breath sample intact and at the same gas concentration distribution. Actual breath sample and bag sample gas concentrations are considered identical if the bag contents are tested within 6 hours of the breath collection. To evaluate for the presence of the COVID-19 disease, gases which provide useful information are nitric oxide (NO), ammonia ($NH_3$) and isoprene (2-methyl-1,3-butadiene; $C_5H_8$). To adequately monitor for the presence of the virus, and to distinguish certain test results indicating the presence of COVID-19 compared to a distinct ailment, such as the common flu, a sensor array capable of detecting each of NO, $NH_3$, and isoprene is preferred. Or a sensor array containing a nitric oxide sensor and one other sensor device can be employed. A sensor which can only detect NO is still important to the test method because the presence of NO either as an individual gaseous biomarker or as a reaction product provides useful information about the subject's status of health or disease. The sensor for the biomarker generally utilizes a metal oxide semiconductor, such as prepared from $WO_3$ or $MoO_3$ layers deposited onto a substrate. A single sensor highly selective to NO is catalytically active when in the presence of the tungsten oxide semiconductor material under the test conditions.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

FIG. 3 is a cross-sectional diagrammatic view of the breathing sensing unit of FIG. 2 including sensor assemblies each having a sensor.

FIG. 3A is a cross-sectional diagrammatic view of a sensor of FIG. 2.

FIG. 3B is a top-view of the sensor of FIG. 3A.

FIG. 4 is a perspective view of the sensor assemblies of FIG. 3.

Figure 1:
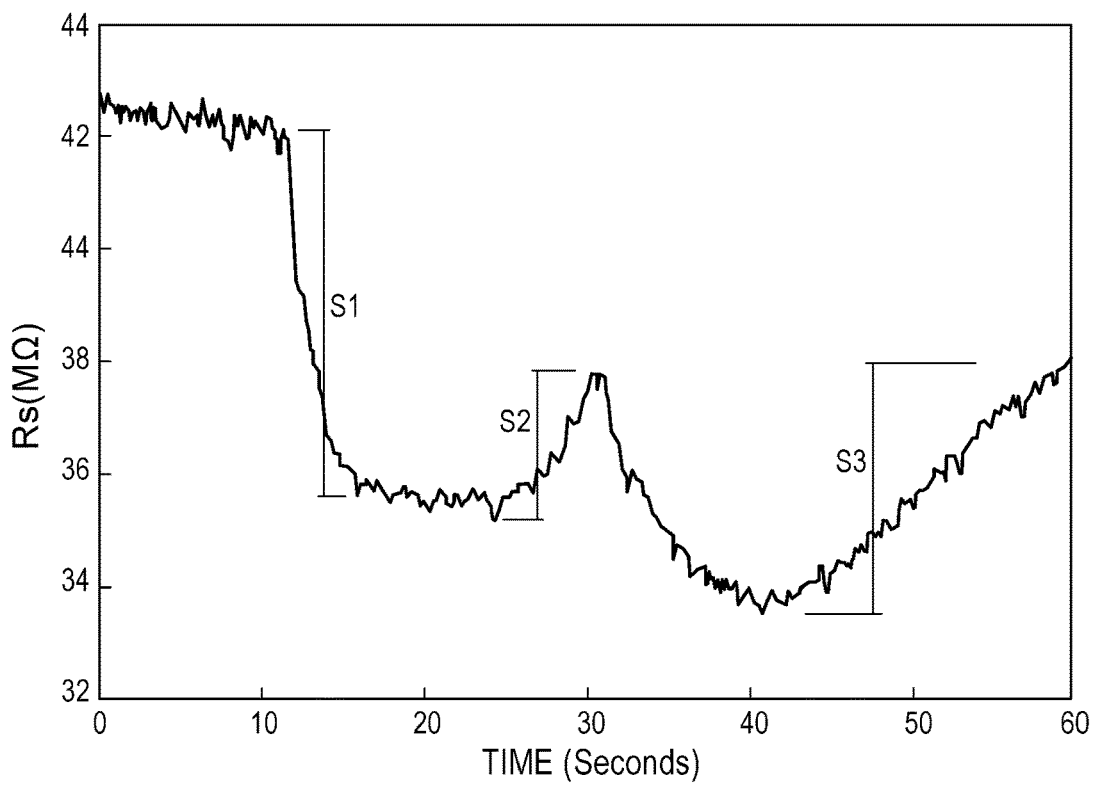
FIG. 1 is a graphical view illustrating a resistance versus time for a breathalyzer in accordance with an embodiment of the invention.

It should be understood that the appended drawings are not necessarily to scale, and may present a somewhat simplified representation of various features illustrative of the basic principles of the invention. The specific design features of the sequence of operations disclosed herein, including, for example, specific dimensions, orientations, locations, and shapes of various illustrated components, may be determined in part by the particular intended application and use environment. Certain features of the illustrated embodiments may have been enlarged or distorted relative to others to facilitate visualization and a clear understanding. In particular, thin features may be thickened, for example, for clarity or illustration.

DESCRIPTION OF THE INVENTION

To address the issue of COVID-19 test result delays and obviate the risk of false test results from either the molecular test or the antigen test, a test to evaluate for the presence of the COVID-19 disease in a subject is performed utilizing a breath analyzer unit (also identified herein as a breathalyzer). The breathalyzer can perform an analysis of gaseous biomarkers resulting from metabolic changes occurring in the body as a result of the infection by the virus. The unit detects gaseous biomarkers in a subject's breath which, in turn, would signal the presence and the severity of the infection caused by the SARS-CoV-2 virus.

Testing using the breathalyzer begins with the subject either providing a single breath exhale into the device, or alternatively filling a breath bag which then provides a six-hour lifetime of maintaining the breath sample intact and at the same gas concentration distribution. Actual breath sample and bag sample gas concentrations are identical if the bag contents are tested within 6 hours of the breath collection. To evaluate for the presence of the COVID-19 disease, gases providing useful information are nitric oxide (NO), ammonia ($NH_3$) and isoprene (2-methyl-1,3-butadiene; $C_5H_8$). To adequately monitor for the presence of the virus, and to distinguish certain test results indicating the presence of COVID-19 compared to a distinct ailment, such as the common flu, a sensor array capable of detecting each of NO, $NH_3$, and isoprene is preferred. Or a sensor array containing a nitric oxide sensor plus a sensor for either $NH_3$ or isoprene is an alternative. A sensor which can detect NO is relevant to the test method because the presence of NO, both as an individual gaseous biomarker or as a reaction product, provides useful information about the subject's status of health or disease. The sensor may detect NO only.

The γ-phase of a $WO_3$ metal-oxide when fabricated into a sensor is sensitive to NO, and sensor resistance is proportional to the NO concentration, producing a digital readout (output signal) which varies based on the NO concentration of the subject's breath sample. To sense the concentration of an analyte and provide a graphic output, the change in the resistance of the sensor over testing time is converted to a pattern on a graphic display (signal). The tungsten oxide semiconductor is catalytically active under the test conditions.

The sensor (which material consists of pure, nanostructured γ-phase $WO_3$ on Pt electrodes deposited on an alumina substrate) enables the catalytic oxidation of ammonia to NO, among other species and the non-catalytic oxidation of ammonia to other species. These catalytic reaction sequences contribute to creating a unique pattern for the change in the electrical resistance of the NO sensor with two minima and a maximum (resembling the small Greek letter omega (ω)). Further reference herein to an omega resistance pattern, or to an omega pattern, or omega breath print, relates to this electrical resistance pattern as graphically depicted.

The ammonia content of the subject's breath sample, plus that of urea, is known to be elevated in COVID patients based on data from other studies. Further, NO levels are expected to rise in individuals who contract COVID, even if they are asymptomatic. As a result, the breathalyzer-facilitated evaluation of NO content is useful in monitoring for the presence of the disease in individual subjects, even before the subject shows symptoms of having contracted the disease. In addition, the third biomarker, isoprene, is a relevant gas to monitor because studies have found that pneumonia is an equivalent to high-altitude pulmonary edema (HAPE), and isoprene is a biomarker associated with early detection of HAPE. Also, isoprene is a biomarker for the presence of common flu. Graphic distinctions which would be observed between patient testing for COVID, HAPE, and flu symptoms mean that the ability to monitor for isoprene and evaluate those results in tandem with the γ-$WO_3$ sensor provides another indication of the presence of either the COVID-19 infection or another ailment. Similarly, the ability to directly measure a resistance related to the presence of ammonia is not vital to an evaluation for the presence of COVID, but it does support the process of diagnosing COVID in the subject relative to other maladies.

Compared to existing molecular and antigen tests, the breathalyzer monitoring process is also substantially faster. The output waveform/breath print produced by the breathalyzer circuitry, if the COVID disease is present, will generate two minima and one intermediate maximum over a continuous curve. These data can then be further analyzed, the data stored, and optionally transferred to a data monitoring/storage location via wireless means such as via Bluetooth technology. The analysis of the breath sample can occur in as little as 15 seconds, and the sensor can cycle every minute, allowing for up to 60 patient analyses per hour, though more practically, the sampling rate would be somewhat lower, on the order of 30 analyses per hour.

The breathalyzer sensor unit requires a power source to create the temperature needed to activate the semiconducting response of the sensing element. Temperatures on the order of about 300° C. to about 550° C. are necessary for the NO sensors. The isoprene sensor operates between 150° C. and 260° C. The ammonia sensor operates at about 500° C. or above. The individual sensors can maintain their discrete operating temperature ranges on the array with creation of sufficient distance, use of inert insulating material, or combinations thereof. The power source can optionally be a rechargeable battery, though other energy sources are possible. At a required operating voltage of about 4.5 to 5 V and a heater supply current of 200 mA, it is believed that approximately 500 measurements could be conducted between battery charges. The number may increase by pulse-width modulating the heater supply voltage. And, using micro-hotplate heaters can reduce the power consumption, thereby also reducing the supply voltage requirements below 3 V.

As indicated above, the determination of biomarker concentration is facilitated by the use of one or more gaseous sensors which are arrayed in the breathalyzer unit. These sensors provide a response to the presence of the respective gaseous biomarker manifested as a change in the electrical resistance of each sensor as a function of both the presence of a biomarker and its concentration.

To prepare the sensor specific to NO, a device was made using a sol-gel process using tungsten ethoxide as a precursor.

The sensor made by a sol-gel process was connected to a TO-8 stamped transistor outline header package through gold wires (Alpha Aesar, 0.25 mm diameter, 99.998%) bonded on integrated platinum circuits on an $Al_2O_3$ substrate, as shown in FIGS. 3-4.

Another method to use the sol-gel material for a NO sensor is to utilize a flame spray pyrolysis system such as a desktop lab-scale nano powders production system from TETHIS (NCP-10). The NCP 10 system contained three main parts: a nozzle unit, a dispensing system and a control unit, all located in a lab vented fume hood. The system was controlled by computer. The collecting system was based on glass fiber filters on the top of the collecting chamber.

The precursor solution was prepared in the following way: 0.3 M of tungsten (VI) isopropoxide (99% ALLCHEMIE) was dissolved in 2-propanol in a nitrogen atmosphere glovebox. After aging for a day, the precursor was supplied at a rate of 5 mL/min through the flame nozzle and dispersed by oxygen at a rate of five standard liters per minute (slm) to form a fine spray. This fine spray was ignited and supported by the flame that was the combustion product of methane and oxygen at the rate of 1.5 slm and 3.0 slm, respectively. The synthesized particles were deposited beneath a glass fiber filter (WHATMAN) and collected. Alternatively, tungsten ethoxide can be used in place of tungsten (VI) isopropoxide.

The powder material is dissolved in a solvent and deposited on alumina with interdigitated Pt electrodes.

The sensor was connected to a TO-8 stamped transistor outline header package through gold wires (Alpha Aesar, 0.25 mm diameter, 99.998%) bonded on integrated platinum circuits on an $Al_2O_3$ substrate, as shown in FIGS. 3-4. The heater was mounted below the sensor in the same package and adhered to the sensor using alumina paste to improve the heat conduction. The operating temperature of the NO sensor throughout the experiments was kept constant, within a few degrees of the set temperature.

In the matter of creating the three-sensor array, a sensor able to detect isoprene is one part of the sensor array. Isoprene: 2-methyl-1,3-butadiene ($C_5H_8$) is a reactive aliphatic hydrocarbon and a VOC marker of the flu. Although more than 1000 kinds of VOCs have been found in human breath, only a few exist in all human bodies. Among them, isoprene is the most common one, which is always present as a precursor of many relevant organic compounds during the metabolic process.

The acid precipitation method was used to synthesize the h-$WO_3$ material. A detailed description is as follows: 1.17 g of $Na_2WO_4 \cdot 2H_2O$ of analytical grade was dissolved in 17 mL of water and the solution was cooled to 10° C. To this, 8.4 mL of normal hydrochloric acid solution (analytical grade, 18% in excess of equimolar reaction) cooled to the same temperature was added in one dose. The mixture is put back into the refrigerator and allowed to stand for about 20 hours. The following reaction occurs:

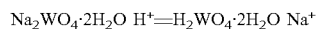

$$Na_2WO_4 \cdot 2H_2O\ H^+ = H_2WO_4 \cdot 2H_2O\ Na^+$$

After this time, the whole mixture turned to a whitish gel. Then, 110 mL of water was added to the vessel, and the gel and water were lightly stirred manually. By centrifuging the supernatant liquid was removed. Then, 130 mL of water was added to the precipitate, and the steps of light manual stirring, centrifuging, and removal of supernatant liquid were repeated several times to obtain $H_2WO_4 \cdot H_2O$, the precursor of the final h-$WO_3$ powders. $H_2WO_4 \cdot H_2O$ suspensions were passed to hydrothermal dehydration and carried out in Parr acid digestion bombs at 125° C.±5° C. Dehydration occurred under air. The furnace temperature was 300-330° C. The annealing time was 90 min.

The color of the synthesized h-$WO_3$ is grey. There are typically two shapes of grains: equiaxed particles and rod-shaped particles. These two shapes are mixed together, and the rods are the majority. There is a certain dispersion of the diameter distribution, from 20 to 50 nm, with an average size of 35 nm. The HRTEM image and the SAED pattern confirm that these particles are polycrystalline and can be indexed in the h-$WO_3$ structure. The diameters of the rods are 30-100 nm with an average value of 50 nm, and their lengths are up to 100-300 nm with an average value of 200 nm. The HRTEM image clearly records the lattice of the h-$WO_3$ (001) planes with an interplanar spacing of about 0.39 nm, indicating the $WO_3$ rods are single crystalline in most regions and grow along the [001] direction, which is in accordance with the SAED pattern.

A heat treatment was usually necessary for the sensor to become stable, e.g., to remove the residual tungsten hydrate by-product. For h-$WO_3$, the heat treatment was done at 350° C. for 8 hours. h-$WO_3$ showed a sensitive and selective detection of isoprene at 350° C. The sensitivity of h-$WO_3$ sensor to isoprene is 7.34, which is higher than any other gas.

The ammonia sensor was made by a sol-gel process but any other method that produces the alpha-phase of $MoO_3$ may be used. As an example of the fabrication process, a sol-gel synthesis method was employed to produce 3D networks of $MoO_3$ nanoparticles through an alkoxide reaction between molybdenum isopropoxide and 1-butanol. The prepared sol was spin-coated onto sensing substrates (3 mm×3 mm alumina plated with interdigitated Pt electrodes) producing thin films of $MoO_3$. The amorphous films were then calcined at 500° C. for 8 hr to form the α-$MoO_3$ polymorph.

The sensor was tested using a gas-flow bench. The gases used were UHP (ultra high purity) nitrogen (Praxair), UHP oxygen (Praxair), 10 ppm ammonia in $N_2$ (NORLAB gases). $NH_3$ concentration was varied by varying its flow rates in connection with $N_2$ and $O_2$ flow rates. The gases were controlled through 1479 MKS Mass flow controllers whose channels are connected to a Type 247-MKS 4-channel readout which reads the flow rate of the gases directly in sccm (standard cubic centimeter per minute). The combined flow rate of the gases was maintained at 1000 sccm. A schematic of the sensor on a TO8 substrate, the sensing chamber and the gas sensing set up are given in FIGS. 2-5.

The effect of humidity was evaluated using a controlled humidity chamber, in which relative humidity can vary between 0 and 100% in the presence of the gas under study. Humidity is produced by bubbling $N_2$ gas stream through a standard water bubbler at room temperature. The percentage of humidity was controlled by varying the ratio of dry to wet $N_2$. A commercially available $CO_2$ filter (NaOH premixed with Vermiculite in a 10:1 ratio—Decarbite absorption tube, PW Perkins and Co) was used in these studies. Decarbite reacts only with highly acidic gases such as $CO_2$, $H_2S$.

Furthermore, a portable breath analyzer was developed by attaching a heater to the backside of the sensor's substrate and then embedding them into a circuit board.

The sensing element used to detect ammonia was a nanocrystalline, sol-gel processed thin film of a semiconducting ceramic, $MoO_3$. This metal oxide, which is also a known catalyst, has been stabilized in its $\alpha$-phase polymorph with an orthorhombic crystal structure. The $\alpha$-$MoO_3$ phase has a layered structure with (010) basal plane that is built up of double chains of edge-sharing $[MoO_6]$ octahedra connected through vertices. Upon reduction in catalytic reaction with gases this phase forms the $MO_{18}O_{52}$ structure instead of the $ReO_3$ type $MO_8O_{23}$ shear structure. The $\alpha$-phase is selective to ammonia and highly sensitive to amines (which are moderate bases) and the sensing mechanism is consistent with the reduction of $MoO_3$ and the formation of ordered phases, which suggests a reaction-based sensing process. This was true for sputtered films, as well as for sol-gel processed ones. Regardless of the processing method used, the $\alpha$-phase exhibited a trend of selective response to ammonia in the presence of interfering gases. Furthermore, this observed selectivity included gases that were typically encountered in the human breath, including $NO_2$, NO, $C_3H_6$, and $H_2$; there was a slight cross-sensitivity for sol-gel processed films to CO (for tested concentrations between 50-500 ppm).

The nanocrystalline $\gamma$-phase tungsten trioxide ($WO_3$) used to form the sensor has a unique property by which its electrical resistance increases in the presence of nitric oxide (NO) gas. Other gases may be present in the subject's breath sample such as isoprene, acetone, and other carbon-containing gases, but the NO sensor does not respond to these. Under the conditions found at the surface of the $\gamma$-phase $WO_3$ sensor, including the presence or absence of oxygen from the subject's exhaled breath, several oxidizing reactions may be taking place, though at different rates. The $\gamma$-phase $WO_3$ sensor temperature is in the range of 300° C. to 350° C. in preparation for conducting the breath analysis.

Under the breathalyzer's operating parameters, the $\gamma$-phase $WO_3$ sensor surface responded primarily to the presence of nitric oxide (NO) and how its concentration changed due to the presence of ammonia ($NH_3$). For comparative purposes, a sensor for ammonia can be an active part of the sensor array, using $\alpha$-$MO_3$ as the sensing material, but it is not necessary.

Prior to the subject's exhaled breath being detected using the sensor, a base line resistance was determined by the ambient air in the receiver (sensing chamber) being sensed by the $\gamma$-phase $WO_3$ sensor. When the subject's exhaled breath enters the receiver/sensing chamber and passes over the heated sensor, the sensor detects the presence of NO, the intensity of signal being a function of concentration.

NO in the receiver is not only present from the NO in the subject's breath. The NO may also be present resulting from the catalyzed oxidation of ammonia on the surface of the sensor in the presence of ambient air oxygen. NO may also form from $NH_3$ in the elevated temperature environment of the receiver.

Referring to FIG. 1, and not wishing to be bound to a specific mechanistic explanation, the resistance due to the presence of NO and observed as an output from the $\gamma$-phase $WO_3$ sensor on the alumina substrate initially drops, but then increases. This is due to the non-selective oxidation of ammonia and the rise in the resistance is due to the selective oxidation. So the resistance then drops a second time, and again increases. The particular tracing of these NO concentration changes approximates the appearance of the Greek letter "omega" ($\omega$) and correlates to subjects known to have the COVID disease. Subjects who do not have the COVID disease display a NO resistance-related pattern which is a single peak, the intensity of which is proportional to the concentration of NO in breath. The omega pattern traced out from a subject's breath sample passing over a $\gamma$-phase $WO_3$ sensor in a heated receiver/sensing chamber is thus an indicator of the presence of the disease. And, as the subject recovers, the peak of the omega pattern reduces in height, believed to indicate that the concentration of ammonia in the exhaled breath is lower, the higher amount of ammonia thus indicating the subject was in the earlier stages of the disease. Thus, in the presence of a single NO sensor, this specific resistance-related pattern can be generated.

A sampling of patients was evaluated using a breathalyzer fitted with a nitric oxide sensor assembly. Forty-six patients were evaluated; 23 were previously diagnosed with COVID-19 and 23 were COVID-19 negative control patients. Because of a sensor failure, the test included a total of 39 patients. There were a priori assumptions with this sample group to give an 80% power to detect a 50% increase in exhaled nitric oxide in the COVID-19 infected individuals with an $\alpha$=0.05. Discrete variables were analyzed using the Pearson Chi-square test. Continuous variables using either Student's T-Test or Wilcoxon Rank Sum analysis were evaluated depending on distribution. All analysis was performed on a JMP Pro 14.0.0 (SAS Institute Inc.).

The signature pattern was plotted using the breathalyzer system. Specific to the COVID-19 infections, the omega pattern appeared as a breath print (see FIG. 1). This pattern resulted from the interaction between oxygen, nitric oxide, and ammonia of the breath gas.

Demographic information was also evaluated for breath gas biomarker variations that might have been due to a distinct pre-existing condition. Analysis with the breathalyzer demonstrated the omega pattern in 14 of 16 patients who were positive for COVID-19 on study day 1. The negative predictive value of the breathalyzer was excellent at 90%. The study length was 10 days, and among the COVID-19 positive patients that remained on a ventilator for all 10 days, there was a general trend in the decrease of the amplitude of the omega S2 peak over the course of the illness until transitioning to the NO pattern.

As indicated above, the breathalyzer can further include an additional sensor, sensitive to the biomarker isoprene, which can assist medical personnel in evaluating the status of a patient who may have symptoms which could be interpreted either as being related to COVID or, alternatively, influenza. There can also be a discrete ammonia sensor included in the breathalyzer, as desired, to independently monitor the ammonia content or being used to differentiate a third disease.

The sensing element for ammonia detection was a nanocrystalline—sol-gel processed thin film of a semiconductive ceramic, $MoO_3$. The alpha phase of $MoO_3$ was selective to ammonia, forming three dimensional networks.

The particular sensor was semi-conducting at elevated temperatures only in the alpha phase.

Isoprene was detected by the use of the sensor produced from an unstable hexagonal phase tungsten trioxide ($h-WO_3$). The sensor material can be produced using an acid precipitation method.

Turning to the figures, FIG. 1 depicts a graph of sensor resistance $R_S$ versus time for an exemplary breath-test of a COVID patient. As can be seen, the sensor resistance $R_S$ varies according to the omega pattern described above. Sections S1-S3 show the changes in resistance due to the presence of one or more relevant gasses having a concentration and sequence correlated with a positive result.

Figure 2:
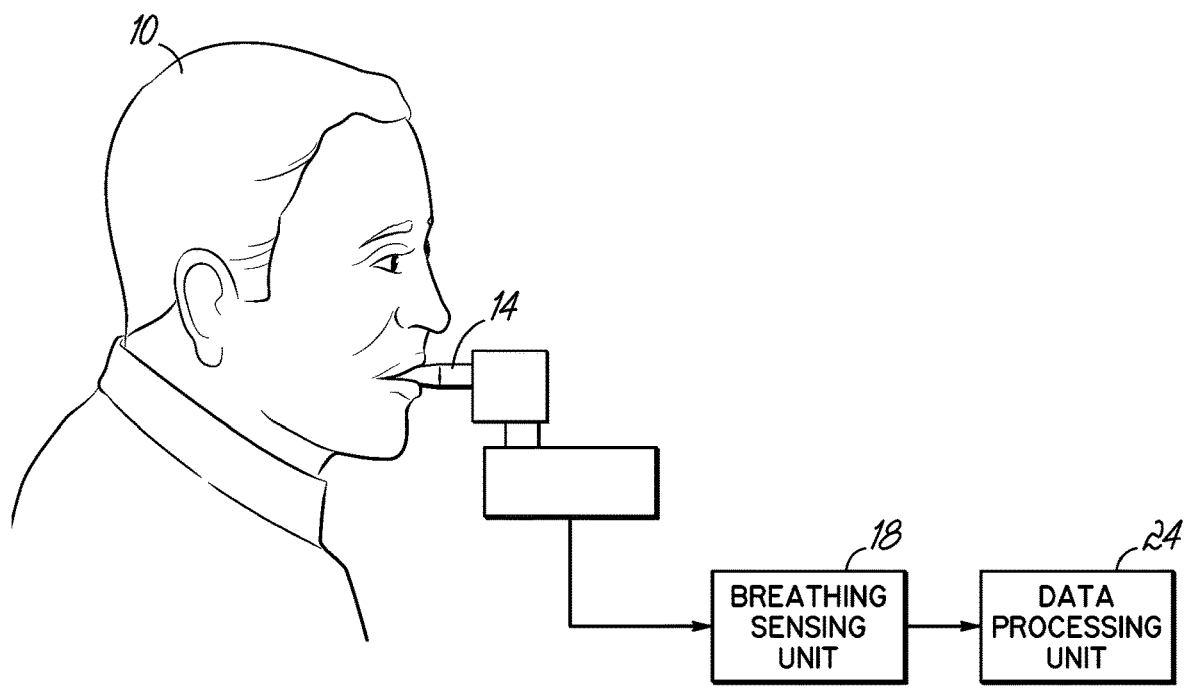
FIG. 2 is a diagrammatic view of a subject 10 blowing into an exemplary breathalyzer including a breathing sensing unit and a data processing unit.

FIG. 2 depicts a subject 10 blowing into a mouthpiece 14. The gasses exhaled by the subject 10 are provided to a breath sensing unit 18 including one or more sensors configured to detect a gas relevant to the test being administered. The one or more sensors are operatively coupled to a data processing unit 24, which generates one or more signals indicative of the sensor resistance $R_S$ of each of the sensors. These signals are then analyzed to generate a test result.

FIG. 3 is a cross-sectional view of the breath sensing unit 18. The breath sensing unit 18 includes a plurality of sensor assemblies 100a, 100b each including a sensing element 110a, 110b operatively coupled to a circuit board 130 by conductors 136. Each sensor assembly 100a, 100b also includes a heater 120a, 120b configured to heat the sensing element 110a, 110b to an operating temperature at which the sensing element 110a, 110b is sensitive to the gas being detected. As the subject blows into the mouthpiece 14, a breath sample 2 passes through the sensing unit 18 and interacts with the sensing element 110a, 110b. It should be understood that the breathing sensing units 18 are not limited to any particular number of sensor assemblies 100a, 100b, and the exemplary breathing sensing unit 18 is merely depicted as having two sensor assemblies 100a, 100b for simplicity and clarity.

FIG. 3A is a cross-sectional view of a sensing element 110a including a non-conductive substrate 112a (e.g., alumina), a sensing layer 114a comprising a sensing material (e.g., $WO_3$, $MoO_3$, or other suitable material having a conductivity that changes in the presence of a relevant gas), and an electrode 116a (e.g., formed from platinum or any other suitable conductive material). FIG. 3B is a top-view of the sensing element 110a, and depicts details of the electrode 116a. The electrodes 116a may have an interdigitated structure, and may be electrically coupled to the sensing layer 114a. The interdigitated structure may increase the length of the region between the two electrodes 116a using an interlocking-finger design for metallization of the electrodes 116a. Although depicted as being on top of the sensing layer 114a for clarity, is should be understood that the electrode 116a may also be located between the substrate 112a and sensing layer 114a.

FIG. 4 is a perspective view of the sensor assemblies 100a, 100b depicting their relationship with the circuit board 130.

Figure 5:
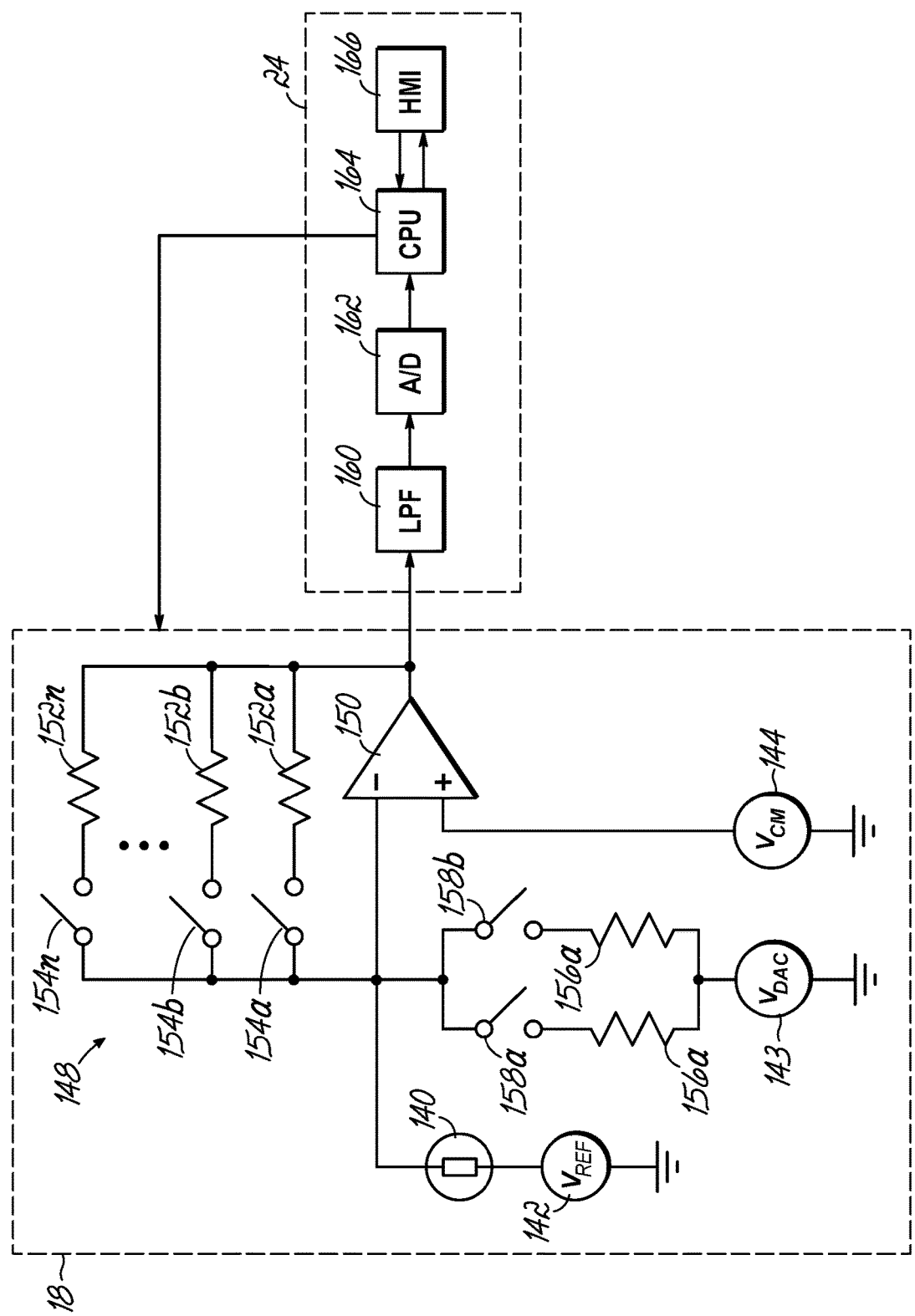
FIG. 5 is a schematic view of the breathalyzer showing additional details of the breathing sensing unit and a data processing unit of FIG. 2.

FIG. 5 is a schematic view depicting a breathalyzer 138 including the breathalyzer sensing unit 18 and data processing unit 24 of FIG. 2. The breathalyzer sensing unit 18 may include at least one sensor 140, one or more reference voltages 142-144, and a front end circuit 148. The front end circuit 148 may be configured to output a voltage $V_{OUT}$ indicative of a resistance $R_S$ of the sensor 140. The front end circuit 148 may include an operational amplifier 150, one or more feedback resistors 152a-152n, which may as well include feedback resistor 152b, one or more feedback switches 154a-154n, which may as well include feedback switch 154b, that selectively couple the feedback resistors 152a-152n between the output of the operational amplifier 150 and an inverting input thereof, one or more calibration resistors 156a, 156b, and one or more calibration switches 158a, 158b that selectively couple the calibration resistors 158a-158b between the non-inverting input of the operational amplifier 150 and a digital to analog converter calibration voltage $V_{DAC}$.

The concentration of the selected gas over the sensor 140 may be quantified by measurement of the sensor resistance $R_S$, which may be the sum of a baseline resistance $R_B$ and a gas resistance $R_G$ that is proportional to the concentration of the selected gas. The baseline resistance $R_B$ is the resistance of the sensor 140 when the selected gas is not present in the environment. The baseline resistance $R_B$ may drift over time, thereby affecting the sensitivity of the measurements. Baseline resistance drift may be compensated for using a calibration procedure incorporated in the breathalyzer 138 to compensate for this variation. The output voltage $V_{OUT}$ may be a non-linear function of the sensor resistance $R_S$, as provided by:

$$V_{OUT} = V_{REF} + \frac{R_F}{R_S}(V_{CM} - V_{REF}) \qquad \text{Eqn. 1}$$

where $R_F$ is the feedback resistance, $V_{CM}$ is the reference voltage at the non-inverting input of the operational amplifier 150, and $V_{REF}$ is the reference voltage at one of the outputs of the sensor 140. By way of example only, the voltages $V_{CM}$ and $V_{REF}$ may be set to 1.5 V and 0.5 V. The sensitivity of the conversion may depend on the resistance value:

$$\frac{dV_{OUT}}{dR_S} = \frac{R_F}{R_S^2}(V_{CM} - V_{REF}) \qquad \text{Eqn. 2}$$

Because the output voltage $V_{OUT}$ may have a limited range insufficient to adequately cover the whole range of the sensor resistance $R_S$, the feedback resistance $R_F$ may be programmable, and the gas resistance $R_G$ measured across different ranges set by the value of the feedback resistor $R_F$. The number of different feedback resistors and their values may be set in order to achieve a desired resolution (e.g., 12-bits) in the measurement of the gas resistance $R_G$ over the full range. In a single measurement range, the minimum value of the sensor resistance with respect to the value of the feedback resistance that can be observed is defined by the maximum output voltage of the operational amplifier 150:

$$\frac{R_S^{MIN}}{R_F} = \frac{V_{CM} - V_{REF}}{V_{MAX} - V_{CM}} S_{Rs} \qquad \text{Eqn. 3}$$

Because the op-amp 150 has a rail-to-rail output voltage, the maximum output voltage $V_{MAX}$ may be limited to a maximum amount, e.g., 4.5 V for a 5 V positive power supply voltage. The maximum value in a single measurement range may be set to provide a desired resolution of the resistance conversion, as the sensitivity may be at a minimum for the maximum value of the sensor resistance. The maximum resistance that can be measured in specific range $R_{MAX\_S}$ with respect to the feedback resistor may be expressed as the function of the resolution of the conversion of the sensor resistance $S_{Rs}$:

$$\frac{R_S^{MIN}}{R_F} = \frac{V_{CM} - V_{REF}}{V_{LSB}} S_{Rs} \qquad \text{Eqn. 4}$$

where $V_{LSB}$ is the voltage of the least-significant bit (e.g., out of 16 bits) in an analog-to-digital conversion of the output voltage, assuming that the analog to digital converter has a full range of 5 V. For the chosen values of the reference voltages, the ratio of the minimum sensor resistance to feedback resistor may be ⅓, while the ratio of the maximum sensor resistance to feedback resistor for 12-bit resolution may be 3.2.

When the value of the sensor resistance $R_S$ reaches the limit of the a particular range, the value of the feedback resistor may be changed by the central processing unit selectively activating one or more of the feedback switches 154a-154n. To guarantee the continuity of the measurement, the ranges may be designed to have a predetermined overlap (e.g., 10% overlap). To cover the full range of the sensor resistance and to maintain a desired resolution (e.g., 12-bit resolution), the different values that the resistor $R_F$ may be set to may include exemplary impedances 4.99 kΩ, 49.9 kΩ, 450 kΩ, 4 MΩ, and 33 MΩ.

The data processing unit 24 may include a low pass filter 160 (e.g., a second-order unity-gain Sallen-Key filter with a cut-off frequency of 19 Hz), an analog to digital converter 162 (e.g., a 8 to 16 bit converter with a sample rate>40 Hz), a central processing unit 164, and a human machine interface (HMI) 166.

The front-end circuit 148 may comprise a programmable trans-resistance amplifier that converts the sensor resistance $R_S$ to voltage. This voltage may then be filtered by the low-pass filter 160. For a specific sensor 140 operating at a specific temperature, the variation of the sensor resistance should not exceed two orders of magnitude. However, the front-end circuit may be used with different sensors that can operate at different temperatures. Thus, the sensor resistance $R_S$ can vary over a wide range, e.g., from 2 kW to 100 MW.

The systematic sources of error in the measurement of the sensor resistance may include an imprecision in the value of the feedback resistors 152a-152n, the voltage offset of the operational amplifier 150, and the current offset through the feedback resistors 152a-152n stemming from the leakage currents of the switches 154a-154n and the input current of the operational amplifier 150. In order to minimize the effect of finite resolution of the feedback resistors 152a-152n, high precision resistors may be used as the calibration resistors 156a, 156b. However, in the higher ranges of the feedback resistors 152a-152n (e.g., 450 kΩ, 4 MΩ, and 33 MΩ), low tolerance resistors can be prohibitively expensive. In the lower range (e.g., 4.99 kΩ and 49.9 kΩ) low price resistors with 0.01% tolerance are common.

The central processing unit 164 may be configured to perform a calibration procedure before a new sensor 140 is placed in breathalyzer sensing unit 18 to estimate the values of the feedback resistors and voltage and current offsets. One calibration resistors 156a may be a low-tolerance resistor having an impedance that matches the feedback resistor 152a in the lowest resistance measurement range. In the first calibration measurement, the output voltage is measured without the sensor 140 with only the switches in the branches with feedback resistor 152a and calibration resistor 156a being turned on. The deviation from the ideal output voltage in this range may be dominated by the voltage offset of the operational amplifier 150, while the effect of the current offset and the finite resolution of the feedback resistor 152a can be neglected.

From the measured output voltage, a value of the voltage offset may be estimated. Another calibration resistor 156b may have a value, for example, of 100 kΩ with 0.01% tolerance. The central processing unit 164 may perform measurements of the output voltage $V_{OUT}$ in the highest sensor resistance measurement range with only the feedback and calibration switches 154n, 156b activated in the branches with the highest impedance feedback resistor 154n and the high impedance calibration resistor 156b. From these two values, the central processing unit 164 may estimate the current offset and the deviation of the high-impedance feedback resistor 152n from its ideal value. Single output voltage measurements in two other resistance ranges may provide estimates of the deviation of any additional non-precision feedback resistors from their ideal values.

The central processing unit 164 may comprise a computing device that includes a processor and a memory. The processor may include one or more devices that manipulate signals (analog or digital) based on operational instructions stored in memory. Memory may include a single memory device or a plurality of memory devices capable of storing data. The processor may operate under the control of an operating system that resides in memory. The operating system may manage central processing unit resources so that computer program code embodied as one or more computer software applications residing in memory can have instructions executed by the processor. One or more data structures may also reside in memory, and may be used by the processor, operating system, or application to store or manipulate data.

The human machine interface 166 may be operatively coupled to central processing unit 164 to allow a user to interact directly with the breathalyzer 138. The human machine interface 166 may include video or alphanumeric displays, a touch screen, a speaker, and any other suitable audio and visual indicators capable of providing data to the user. The human machine interface 166 may also include input devices and controls such as an alphanumeric keyboard, a pointing device, keypads, pushbuttons, control knobs, microphones, etc., capable of accepting commands or input from the user and transmitting the entered input to the central processing unit 164.

While the present disclosure has been illustrated by the description of specific embodiments, and while the embodiments have been described in considerable detail, it is not intended that the scope of the appended claims be restricted or in any way limited to such detail. The various features discussed herein may be used alone or in any combination within and between the various embodiments. Additional advantages and modifications will readily appear to those skilled in the art. The present disclosure in its broader aspects is therefore not limited to the specific details, representative apparatus and methods and illustrative examples shown and described. Accordingly, departures may be made from such details without departing from the scope of the present disclosure.

Having described the invention, what is claimed is:

1. A method of evaluating for a presence of a COVID disease in a subject, the method comprising:
    collecting a breath sample from the subject,
    passing the breath sample over at least one sensor that is selective to a NO breath gas biomarker, and
    collecting a signal ($V_{OUT}$) generated by the at least one sensor displayed as a pattern of resistance change over time, wherein the presence of the COVID disease in the breath sample produces an omega pattern from the signal.

2. The method of claim 1, wherein the at least one sensor is sensitive to changes in resistance associated with the NO breath gas biomarker to which the at least one sensor has a selective response.

3. The method of claim 1, wherein the at least one sensor contains a form of tungsten oxide and/or molybdenum oxide.

4. The method of claim 1, wherein the at least one sensor is configured to detect a second biomarker, the second biomarker comprising ammonia.

5. The method of claim 4, wherein the at least one sensor comprises a semiconducting α-$MoO_3$ selective to ammonia.

6. The method of claim 1, wherein the at least one sensor is configured to detect a second biomarker, the second biomarker comprising isoprene.

7. The method of claim 6, wherein the at least one sensor comprises a semiconducting h-$WO_3$ selective to isoprene.

8. The method of claim 1, wherein the at least one sensor is configured to detect a combination of biomarkers, the combination of biomarkers comprising the NO breath gas biomarker, ammonia, and isoprene.

9. The method of claim 1, wherein a single breath exhaled from the subject is collected.

10. The method of claim 1, wherein the method is completed within the range of 15 to 90 seconds.

11. The method of claim 1, wherein collecting the breath sample from the subject comprises collecting the breath sample in a breath bag.

12. The method of claim 1, wherein the at least one sensor is included in a breathalyzer, and the breathalyzer is either handheld or portable.

13. The method of claim 1, wherein the signal may be wirelessly transmitted to a device via an app.

14. The method of claim 1, wherein the at least one sensor comprises a semiconducting γ-$WO_3$.

* * * * *